United States Patent [19]

Ritzer et al.

[11] 4,393,229

[45] Jul. 12, 1983

[54] REDISTRIBUTION OF POLYSILANES IN HIGH BOILING RESIDUES

[75] Inventors: Alan Ritzer, Sand Lake; Abraham L. Hajjar, Scotia; Harry R. McEntee, Waterford; Ray W. Shade, Clifton Park, all of N.Y.

[73] Assignee: General Electric Company, Waterford, N.Y.

[21] Appl. No.: 372,601

[22] Filed: Apr. 28, 1982

[51] Int. Cl.$^3$ .............................................. C07F 7/08
[52] U.S. Cl. .................................... 556/430; 556/469
[58] Field of Search ................................ 556/430, 469

[56] References Cited

U.S. PATENT DOCUMENTS

| | | | |
|---|---|---|---|
| 2,598,435 | 5/1952 | Mohler et al. | 556/468 |
| 2,647,136 | 7/1953 | Sauer | 556/469 |
| 2,647,912 | 8/1953 | Barry et al. | 556/469 |
| 2,681,355 | 6/1954 | Barry et al. | 556/466 |
| 2,709,176 | 5/1955 | Bluestein | 556/468 |
| 2,717,257 | 9/1955 | Bluestein | 556/469 |
| 2,732,282 | 1/1956 | Bailey et al. | 423/342 |
| 2,786,861 | 3/1957 | McEntee | 556/469 |
| 2,842,580 | 7/1958 | Gilbert et al. | 556/472 |
| 2,902,506 | 9/1959 | Gilbert et al. | 556/469 |
| 3,135,778 | 6/1964 | Sleddon | 556/469 |
| 3,322,511 | 5/1967 | Weyenberg | 423/342 |
| 3,769,310 | 10/1973 | Viego et al. | 556/469 |
| 3,793,357 | 2/1974 | McEntee | 556/469 |
| 4,266,068 | 5/1981 | Allain et al. | 556/430 |
| 4,289,890 | 9/1981 | Gordon | 556/430 |

FOREIGN PATENT DOCUMENTS 53-82726  7/1978  Japan ................................. 556/430

OTHER PUBLICATIONS

"J. Organometal. Chem.", 8, pp. 451–458, 1967.
Sakurai et al., Bulletin Chem. Soc., Japan 39, No. 8, 1820, (1966): AlCl$_3$–Catalyzed Reactions of Organosilicon Compounds.
Nagai et al., Chemical Abstracts 88: 105553c, (1978): 1,2-Dimethyltetrachlorodisilane.
Nagai et al., Chemical Abstracts 88: 105556f, (1978): Disilanes.
Nagai et al., Chemical Abstracts, 89: 163733t, (1978): Disilanes.
Nagai et al., Journal of Organometallic Chemistry, 142, 149–153, (1977), A Convenient and Large Scale Synthesis of 1,1,2-Trimethyl-1,2,2-Trichlorosilane and 1,1,2,2-Tetramethyl-1,2-Dichlorodisilane.

*Primary Examiner*—Paul F. Shaver

[57] ABSTRACT

A process is described for converting the alkyl-rich disilanes in the residue obtained from the manufacture of alkylhalosilanes to halogen-rich polysilanes with alkyltrihalosilanes and simultaneously converting the alkyltrihalosilanes to dialkyldihalosilanes by reacting the alkyl-rich polysilanes in the residue and the alkyltrihalosilanes at an elevated temperature in the presence of a suitable catalyst and a catalytic amount of a hydrosilane reaction promoter. In a preferred embodiment, the residue containing alkyl-rich disilanes is treated with methyltrichlorosilane at a temperature of about 100° C. to about 250° C. in the presence of aluminum trichloride catalyst and a catalytic amount of methyldichlorosilane.

34 Claims, No Drawings

REDISTRIBUTION OF POLYSILANES IN HIGH BOILING RESIDUES

BACKGROUND OF THE INVENTION

The present invention relates to a process for making redistribution products in residues containing polysilanes, and more particularly, to a process for converting alkyl-rich polysilanes in residues obtained from the manufacture of alkylhalosilanes, into more valuable products. Typically, when the halogen is chlorine, the useful or more valuable products are such monosilanes as dimethyldichlorosilane, trimethylchlorosilane, methyltrichlorosilane and the like.

In the preparation of alkylhalosilanes, various polysilane products are formed during the reaction and remain in the residue after the separation of the monosilanes. For example, in the commercial method known as the "direct process", in addition to the monosilanes, which in the case of the chloromonosilanes include dimethyldichlorosilane, methyltrichlorosilane, trimethylchlorosilane and the like, there is always obtained a variety of compounds which boil above the monosilanes, that is, above about 70° C., which is hereafter referred to as "residue", high boiling fraction or crude fraction. The "direct process" is well described in the patent literature, for example, in U.S. Pat. Nos. 2,380,995 and 2,488,487. The residue is a complex mixture of compounds that include SiSi and SiOSi linkages in the molecules. Typical residues are described in U.S. Pat. Nos. 2,598,435 and 2,681,355.

In current commercial operations, the methylchlorosilane residues, that is, the residue boiling above the monosilanes, and which is formed, for example, during the reaction of methyl chloride and silicon, is cleaved to yield monosilanes plus a fraction that is noncleavable. The cleavage of the organohalogenopolysilanes is described in U.S. Pat. No. 2,709,176 and U.S. Pat. No. 2,842,580, incorporated herein by reference. U.S. Pat. No. 2,709,176 describes the cleavage of the organohalogenopolysilanes by treating them with a hydrogen halide in the presence of an organic amine compound selected from the group consisting of heterocyclic tertiary organic amines, tertiary organic amines having the formula $R_3N$, where R is a member selected from the group consisting of aryl and alkyl groups, and salts of the tertiary amines of (1) and (2). U.S. Pat. No. 2,709,176 also describes the composition of a typical residue mixture containing the high boiling fraction, that is, the material boiling above the boiling point of dimethyldichlorosilane.

U.S. Pat. No. 2,842,580 also describes the cleavage of organohalogenopolysilanes by treating the organohalogenopolysilanes with a specified class of quaternary halides, such as quaternary ammonium halides and quaternary phosphonium halides. The fraction remaining after cleavage is generally disposed of by incineration. For both economic considerations and disposal considerations, it is desirable to eliminate or substantially reduce the amount of residue disposed of by incineration by converting the non-cleavable fraction of the residue to substituents which are cleavable.

In U.S. Pat. No. 2,598,435, methylhalogenopolysilanes containing silicon-silicon linkages and a silicon-bonded methyl group, were heated at a temperature of at least 250° C., and generally at a temperature from 250° C. to 800° C. to form methylhalogenomonosilanes. In U.S. Pat. No. 2,598,435, it was found that the organohalogenopolysilanes could be degraded to lower molecular weight materials and in no way could have been predicted since it was found that attachment of organic groups to a silicon of a disilane, for instance, hexamethyldisilane, rendered such a compound thermally stable at temperatures as high as 500° C. under pressure, and it was found that this stability decreased markedly if there were both a silicon-bonded hydrocarbon radical and a silicon-bonded halogen atom in the disilane. Thus, the cracking process described in U.S. Pat. No. 2,598,435 applied to halogen-rich polysilanes, for example, chlorine-rich disilanes, but it did not apply to the alkyl-rich polysilanes, for example, methyl-rich disilanes.

The redistribution of organosilanes is disclosed in U.S. Pat. No. 2,647,136 where both alkyl groups and halogen atoms are shifted from one silicon atom to another silicon atom as a result of effecting reaction at a temperature of about 250° C. to 400° C. between a first alkylhalogenosilane and a second alkylhalogenosilane. In U.S. Pat. No. 2,647,136, it was found that there is not only the migration of an alkyl group, but also the migration of a halogen atom, and the reaction proceeds without a catalyst at elevated temperatures. Aluminum chloride was the only catalyst found which would accelerate the reaction. In U.S. Pat. No. 3,793,357 redistribution of alkylhalosilanes wherein alkyl groups and halogen atoms are redistributed from one silicon atom to another silicon atom, is effected by using aluminum chloride catalyst and a catalytic amount of a catalytic promoter having at least one aromatic radical in the silane molecule. Compounds included within the scope of U.S. Pat. No. 3,793,357 include alkylhydrogensilanes, such as methyldichlorosilane, trichlorosilane, dimethylchlorosilane, and the like, in which redistribution can occur. In U.S. Pat. No. 3,135,778, it is disclosed that redistribution had been effected by using aluminum chloride as a catalyst in the presence of a silane containing silicon-bonded hydrogen atoms (hydrosilane) for the redistribution of organosilanes (monosilanes) to effect a redistribution reaction among the end products in order to increase the yields of the desired organosilanes and organohalogenosilanes. In U.S. Pat. No. 2,786,861, alkylchlorosilanes were redistributed in the presence of a catalyst, such as the redistribution catalyst, aluminum chloride, and it was found that the reaction could be carried out at lower temperatures in an advantageous manner over the prior art by the use of a catalytic promoter which catalytic promoter comprised a hydrogen silane. However, it is noted in U.S. Pat. No. 2,786,861 that the redistributions were used for making methyl-rich monosilanes rather than chlorine-rich disilanes. Thus, there is no prior disclosure of improving the amount of useful or more valuable product obtainable from the residues and crude fractions obtained from the manufacture of alkylhalosilanes or of treating alkyl-rich disilane- or polysilane-containing residues to produce redistribution products containing halogen-rich disilanes or polysilanes in said residues. Furthermore, there is no suggestion of simultaneously converting alkyl trihalosilanes to dialkyldihalosilanes while converting the alkyl-rich disilane or polysilane fractions of residues to the halogen-rich disilanes or polysilanes.

SUMMARY OF THE INVENTION

Accordingly, it is an object of the present invention to provide a process for improving the yield of useful products from the residues obtained from the manufacture of alkylhalosilanes.

It is another object of the present invention to provide a process for improving the yield of useful products obtained from residues containing alkyl-rich disilanes or alkyl-rich polysilanes.

It is another object of the present invention to provide a process for improving the yield of useful products obtained from the manufacture of alkylchlorosilanes.

Still another object of the present invention is to provide a process for converting alkyl-rich polysilanes in the residue obtained from the manufacture of alkylhalosilanes to halogen-rich polysilanes with alkyltrihalosilanes while simultaneously converting the alkyltrihalosilanes to dialkyldihalosilanes.

Another object of the present invention is to provide a process for improving the utilization of polysilane values in residues obtained from the manufacture of alkylhalosilanes.

A further object of the present invention is to provide a process for cleaving the halogen-rich polysilane or disilane redistribution products obtained from the alkyl-rich disilane or polysilane values in residues obtained from the manufacture of alkylhalosilanes.

These and other objects of the present invention are achieved by a process for treating alkyl-rich polysilane-containing residues comprising, contacting the residue with alkyltrihalosilane and/or silicon tetrahalide in the presence of a catalyst and a catalytic amount of a hydrosilane reaction promoter at an elevated temperature to produce a redistribution product containing halogen-rich polysilane and dialkyldihalosilane. In certain embodiments, the halogen-rich polysilanes obtained as redistribution products in the residue are cleaved to form halosilanes.

In accordance with the present invention, an alkyl-rich polysilane in the residue obtained from the manufacture of alkylhalosilanes is converted to halogen-rich polysilane with alkyltrihalosilane, and the alkyltrihalosilane is simultaneously converted to dialkyldihalosilane under substantially anhydrous conditions, by reacting the alkyl-rich polysilane in the residue and the alkyltrihalosilane at an elevated temperature in the presence of a suitable catalyst and a catalytic amount of a hydrosilane reaction promoter. Generally in most residues, the polysilanes are disilanes.

As used herein, an alkyl-rich polysilane or an alkyl-rich disilane is a polysilane or disilane having alkyl groups but no halogen atoms or fewer halogen atoms than alkyl groups substituted upon the silicon atoms of the molecule. Generally, a disilane is an alkyl-rich disilane when it has from 0 to 2 halogen atoms and preferably 2 to 6 alkyl groups. As used herein, a halogen-rich disilane or polysilane is a disilane or polysilane having halogen atoms but no alkyl groups or fewer alkyl groups than halogen atoms substituted upon the silicon atoms of the molecule. Generally, the halogen-rich disilane or polysilane has an equal number of halogen atoms and alkyl groups substituted upon the silane atoms of the molecule or has a greater number of halogen atoms than alkyl groups substituted upon the silicon atoms of the silane molecule. Generally, a halogen-rich disilane has 3 to 6 halogen atoms and preferably 0 to 2 alkyl groups substituted upon the silicon atoms of the disilane molecule.

Although the invention relates to any of the halogens substituted upon the alkylhalosilanes or polysilanes and include bromine, chlorine, fluorine and iodine or mixtures thereof, in most embodiments of the present invention, the halogen atom or atoms substituted upon the silicon atom or atoms of the alkylhalosilanes or polysilanes, are chlorine atoms. In preferred embodiments, the process of the present invention is used for converting the alkyl-rich disilanes in the residues obtained from the manufacture of alkylchlorosilane to chlorine-rich disilanes with alkyltrichlorosilane while simultaneously converting the alkyltrichlorosilane to dialkyldichlorosilane. In one of the embodiments in accordance with the present invention, the alkyl-rich disilanes are converted to chlorine-rich disilanes, and the conversion is accomplished by redistribution of the alkyl-rich disilane with a chlorine-rich methylchlorosilane. The chlorine-rich methylchlorosilane is converted to dimethyldichlorosilane, the dimethyldichlorosilane being generally recognized as a more valuable product than the methyltrichlorosilane. Thus, by the conversion or the redistribution of the present invention, the polysilanes and disilanes which are rich in alkyl groups and cannot be cleaved or which can only be cleaved with difficulty, are converted to halogen-rich polysilanes and disilanes, and they become cleavable by conventional cleavage processes. Thus, the fractions of the residue which have heretofore been noncleavable and which have been disposed of by incineration or other means, are now converted to cleavable redistribution products and can be cleaved to yield useful or more valuable products.

By the process of the present invention, a greater fraction of the residues obtained from the manufacture of methylchlorosilanes are converted into useful or more valuable products, and simultaneously, methyltrichlorosilane, which is generally available in excess from the methylchlorosilane reactor in commercial embodiments, is converted into the useful product, dimethyldichlorosilane. The net effect resulting from the present invention is an increase in the yield of desirable products accompanied by a reduction of by-products that require disposal or sale at uneconomical prices. In accordance with the present invention, noncleavable fractions obtained from the manufacture of alkylhalosilanes, are converted to a cleavable form by redistribution with an alkyltrihalosilane and the alkyltrihalosilane is simultaneously converted primarily to dimethyldihalosilane and other desirable products.

As used throughout the specification and claims for the general description of the invention, polysilane and disilane may be used interchangeably.

DETAILED DESCRIPTION OF THE INVENTION

The compositions of residues which are treated in accordance with the present invention are well known in the prior art. Typical of the residues which are treated by the process of the present invention are the crude fractions remaining after the separation of the monosilanes from the processes used to prepare alkylhalosilanes. One of the residues which contains polysilanes and which is treated in accordance with the process of the present invention is derived from the prior art process known as the direct process. The direct process has been described above and is disclosed in U.S. Pat. No. 2,681,355, U.S. Pat. No. 2,598,435 and U.S. Pat. No. 2,488,487. In the direct process, generally an alkyl halide is contacted with silicon or an alloy or mixture of silicon and a metal at an elevated temperature to produce alkylsilanes and alkylhalogenosilanes.

After the alkylsilanes and alkylhalogenosilanes are removed from the reaction product, a residue, high boiling fraction or crude fraction remains. It has been determined in the prior art that valuable fractions remain in the residue, high boiling fraction or crude fraction, and various methods have been employed to utilize the silane values in the residues.

In U.S. Pat. No. 2,709,176 and U.S. Pat. No. 2,842,580, processes are employed for cleavage of polysilanes which are found in the residue. Although the halogen-rich polysilanes can be easily cleaved, it is difficult to cleave the alkyl-rich polysilanes. For example, hexamethyldisilane, chloropentamethyldisilane and 1,2-dichlorotetramethyldisilane are alkyl-rich disilanes which cannot be cleaved by conventional techniques or which can only be cleaved with great difficulty. On the other hand, 1,2,2-trichlorotrimethyldisilane, 1,1,2,2-tetrachlorodimethyldisilane and 1,1-dichlorotetramethyldisilane are disilanes which can be cleaved by the conventional methods more readily than cited alkyl-rich disilanes. Generally, all of the foregoing disilane compounds are found in the residue resulting from the direct process method for preparing alkylhalogenosilanes.

The present invention has general application to alkyl-rich organopolysilanes having the unit structure:

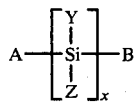

wherein A, B, Y and Z may be any conventional atom or radical, and generally alkyl, halogen, hydrogen and mixtures thereof, and wherein x is an integer of at least 2 and generally an integer from 2 to about 10. Typical residues are shown in U.S. Pat. No. 2,598,435, U.S. Pat. No. 2,681,355, U.S. Pat. No. 2,709,176 and U.S. Pat. No. 2,842,580.

By the process of the present invention, the alkyl-rich polysilanes (alkyl-rich disilanes) are converted to halogen-rich polysilanes (halogen-rich disilanes) by contacting the residue containing the alkyl-rich polysilanes (disilanes) with alkyltrihalosilane and/or silicon tetrahalide in the presence of a catalyst, such as aluminum trichloride and a catalytic amount of a hydrosilane reaction promoter at an elevated temperature to produce a redistribution product containing halogen-rich polysilanes (halogen-rich disilanes) and simultaneously producing a dialkyldihalosilane. For example, when the residue contains hexamethyldisilane, the hexamethyldisilane reacts with methyltrichlorosilane which is an alkyltrihalosilane, in the presence of aluminum trichloride catalyst and in the presence of methyldichlorosilane which is a hydrosilane reaction promoter, to form 1,1,2-trichlorotrimethyldisilane and dimethyldichlorosilane. The chlorine-rich disilane, that is, the 1,1,2-trichlorotrimethyldisilane which is formed in the foregoing reaction, can then be cleaved by any of the conventional methods, such as the reaction with hydrogen chloride, in a residue cleavage process to form useful methylchlorosilanes such as methyldichlorosilane and dimethyldichlorosilane. The dimethyldichlorosilane which is formed in the reaction discussed above, can be distilled from the reaction mixture prior to or after the cleaving of the silicon-silicon bond of the chlorine-rich disilane.

Typical redistribution reactions in the residues described above in accordance with the process of the present invention, which are carried out in the presence of a catalyst, such as aluminum trichloride and a hydrosilane reaction promoter, such as methyldichlorosilane, at an elevated temperature, preferably at a pressure greater than 1 atmosphere in an autoclave, are shown below:

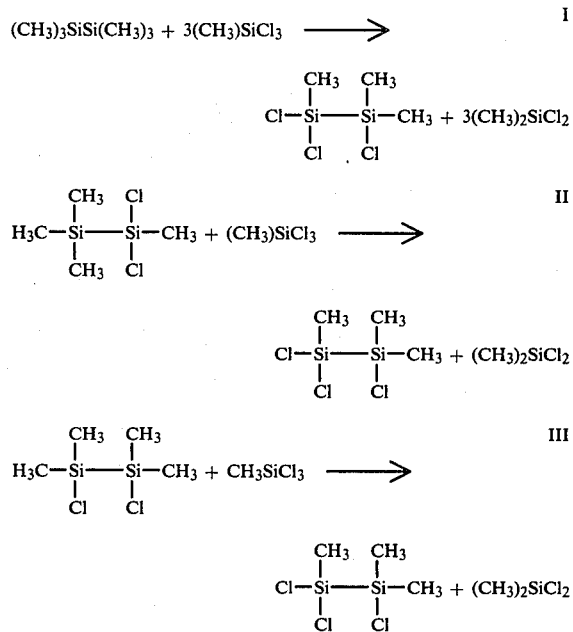

In the foregoing reactions, chlorine-rich disilanes are formed, and these can be more easily cleaved to form monosilanes than their methyl-rich counterparts, and at the same time the methyltrichlorosilane is converted to the more methyl-rich and more valuable dimethyldichlorosilane. It is to be pointed out that other redistributions of similar disilanes and polysilanes occur in the residue composition.

The residue is contacted with, or the disilane portions or fractions of the residue are reacted with, alkyltrihalosilanes and/or silicon tetrahalide in accordance with the process of the present invention. Thus, in the process of the present invention, it is critical to use an alkyltrihalosilane and/or a silicon tetrahalide for the redistribution reaction with the disilanes in the residue. The preferred alkyltrihalosilane is methyltrichlorosilane. The preferred silicon tetrahalide is silicon tetrachloride. Other preferred alkyltrihalosilanes include those having straight chain or branched alkyl groups with 2 to about 8 carbon atoms, and those wherein the halogen atoms are chlorine, bromine, fluorine, iodine, and mixtures thereof. In preferred embodiments, the alkyltrihalosilane is an alkyltrihalosilane produced as a product in the process for manufacturing the alkylhalosilanes, and it can be used directly as a reactant in the process of the present invention. Generally, the alkyltrihalosilane reactant is compatible with the disilanes undergoing the redistribution reaction in the residue, and if the disilanes are chlorinated disilanes, then the alkyltrihalosilane reactant is preferably an alkyltrichlorosilane. Examples of other alkyltrihalosilanes include methyltribromosilane, methyltrifluorosilane, ethyltrichlorosilane, ethyltribromosilane, ethyltrifluorosilane, ethyltriodosilane, n-propyltrichlorosilane, n-propyltribromosilane, n-propyltrifluorosilane, isopropyltrichlorosilane, iso-propyltrifluorosilane, iso-propyltribromosilane, n-butyltrichlorosilane, and the like.

The amount of alkyltrihalosilane may be the stoichiometric amount required to convert the methyl-rich disilane to a chlorine-rich disilane, however, it is generally preferred to use a molar excess of the alkyltrihalosilane to carry out the reaction with the disilanes in the residue. In most preferred embodiments, the alkyltrihalosilane comprises about 0.5 mole to about 4.0 moles per mole of disilane or polysilane undergoing the redistribution reaction in the residue.

Any suitable catalyst which will promote the redistribution of alkyl groups on one silane molecule with halogen atoms on another silane molecule, may be used in the process of the present invention. The preferable catalyst for the process of the present invention is aluminum trichloride or compounds of aluminum trichloride decomposible under the reaction conditions to aluminum trichloride, or any equivalent catalyst which promotes the redistribution of alkyl groups with halogen atoms in the silanes, disilanes and polysilanes. It is preferable to use the catalyst in a concentration of about 1 to about 15 percent by weight based upon the weight of the disilane reactants in the residue and the alkyltrihalosilane, and more preferably, it is desirable to have the catalyst present in a concentration of about 3 to about 10 percent by weight of the reactant mixture, that is, the disilanes and polysilanes in the residue and the alkyltrihalosilane. Examples of other catalysts that may be used in the redistribution reaction of the alkyl-rich disilanes contained in the residues obtained from the manufacture of alkylhalosilanes and the alkyltrihalosilanes are zirconium tetrachloride, potassium aluminum tetrachloride, cuprous chloride, boric acid and boron trifluoride. Generally, any Lewis Acid or its equivalent may be used as a catalyst in the process of the present invention. One skilled in the art can determine the most efficient catalyst to redistribute alkyl groups and halogen atoms depending upon the particular alkyl group and the particular halogen atom without undue experimentation, however, aluminum trichloride is generally the all-purpose catalyst which is more efficient than the other catalysts and which is suitable for redistributing alkyl groups on the silane, disilane or polysilane molecule with halogen atoms on other silane molecules.

Although the above catalysts, and in particular, aluminum trichloride, are effective catalysts for certain redistributions, it has been discovered that a catalytic additive or reaction promoter, as it is defined herein, must be used in conjunction with the above catalysts to obtain the desired redistribution products from the polysilanes including disilanes, in the residues obtained from the manufacture of alkylhalosilanes.

It has been shown that in accordance with the process of the present invention, substantial amounts of halogen-rich disilane or polysilane redistribution products are formed from alkyl-rich disilane or polysilane compounds in residues obtained from the manufacture of alkylhalosilanes when the hydrosilane reaction promoters are used in conjunction with the conventional inorganic catalysts described above, that is, those catalysts which are of the Lewis Acid type catalysts and their equivalents. It has been shown that when aluminum chloride catalyst is used alone without the effect of the hydrosilane reaction promoter, very little halogen-rich disilane compounds are prepared from the alkyl-rich disilanes in the residue.

Any hydrosilane may be used in the process of the present invention as long as it functions synergistically with the inorganic Lewis Acid type catalyst or an equivalent inorganic catalyst to produce halogen-rich disilane redistribution products from alkyl-rich polysilanes and disilanes in the residues described above. The hydrosilane reaction promoters are generally monomeric monosilicon compounds containing as Si-H linkage, and they may contain additional groups or radicals or atoms which will not inhibit the redistribution reaction or the effect caused by the use of the 2 types of catalysts used herein, attached to the silicon atom. It is critical that the reaction promoter have at least one hydrogen atom attached to the silicon atom. Among the hydrosilane compounds having the Si-H linkage are, for instance, those corresponding to the general formula $R_nSiH_{(4-m-n)}Cl_m$, where R is an alkyl radical, an aryl radical or substituted alkyl or aryl radicals, and m and n are integers equal to from 0 to 3, and the sum of m and n is equal to at most 3. Typical hydrosilane reaction promoters which may be used in accordance with the process of the present invention, include phenyldichlorosilane, dimethylchlorosilane, that is, $(CH_3)_2SiHCl$, methyldichlorosilane, trichlorosilane, dichlorosilane, that is, $H_2SiCl_2$, monochlorosilane, trimethylsilane, silane, that is, $SiH_4$, ethyldichlorosilane, and the like. In the above general formula for hydrosilane reaction promoters, R also includes other monovalent hydrocarbons or halogenated monovalent hydrocarbon radicals, such as, chlorinated monovalent hydrocarbon higher alkyl radicals, for instance, octyl, nonyl, pentyl, butyl, propyl, isopropyl, and the like; alkaryl radicals, such as tolyl, xylyl, ethylphenyl, and the like; aralkyl radicals, such as benzyl, phenylethyl, and the like; cycloaliphatic, such as cyclohexyl and the like. Examples of halogenated radicals which may be employed for the R group of the foregoing formula, are halophenyl radicals, such as dichlorophenyl, fluorophenyl and the like. Generally, the preferred hydrosilane reaction promoter is methyldichlorosilane.

Any catalytically effective amount of hydrosilane reaction promoter may be used in the process of the present invention. Thus, any amount of hydrosilane catalytic promoter which results in the formation of halogen-rich disilane or polysilane redistribution products when it is used with a catalytic amount of aluminum trichloride or any other suitable Lewis Acid or its equivalent type catalyst, may be used. Generally, the hydrosilane reaction promoter comprises 0.01 to about 50.0 mole percent based on the moles of the reaction ingredients excluding the aluminum trichloride or other inorganic catalyst. More preferably, the concentration of the hydrosilane reaction promoter is from 1 to about 15 mole percent based on the moles of the reaction ingredients excluding the inorganic catalyst. In the most preferred embodiments, the hydrosilane reaction promoter may be present at a concentration of about 5 to about 10 mole percent based on the moles of the reaction ingredients excluding the inorganic catalyst, such as aluminum trichloride. Optimum amounts of proportions of hydrosilane reaction promoter can be chosen without undue experimentation by observing the yields of desired chlorine-rich disilanes by means of vapor phase chromatography analysis. As used herein, reaction ingredients comprise the disilane or other polysilane and the alkyltrihalosilane.

It should be pointed out that the hydrosilane reaction promoter is a true catalytic promoter, that is, the same hydrosilane reaction promoter may be used in batch after batch with desirable high yields of the desired redistributed disilane or polysilane products. Furthermore, the inorganic catalyst, such as the Lewis Acid type catalyst or its equivalent inorganic catalysts, may also be reused and recycled in accordance with the process of the present invention.

In the process of the present invention, the temperature at which the reaction may be carried out, may be varied, however, the reaction is usually carried out at an elevated temperature, such as at a temperature above ambient temperature. In most cases, the reaction is carried out at a temperature above 50° C. Although there is no upper limit for the reaction temperature, except that it is desirable not to exceed those temperatures where decomposition of the components of the reaction mixture occurs, the upper limit for the reaction temperature is preferably about 250° C. Generally, when the reaction is carried out above 250° C., then unduly large pressures are required in the reactor so as to maintain the reactants in a liquid state and to prevent the catalyst materials from sublimating. In most preferred embodiments, the elevated temperature at which the residue is contacted with alkyltrihalosilane in the presence of a catalyst and a catalytic amount of hydrosilane reaction promoter is between about 100° C. and about 175° C.

Although the process of the present invention can be carried out at atmospheric pressure, it is generally desirable to contact the residue with the alkyltrihalosilane in the presence of the catalyst and the hydrosilane reaction promoter at a pressure greater than atmospheric pressure (super-atmospheric pressure). Thus, the process may be carried out in an autoclave or another similar device capable of withstanding both heat and pressure. In certain preferred embodiments, the process is carried out at a pressure of about 1 atmosphere to about 3 atmospheres. Alternatively stated, in certain preferred embodiments, the reaction may be carried out at a pressure of about 10 to about 100 lbs./sq. in. gauge. Again, the reaction may be carried out at higher pressures, however, this necessitates the use of expensive reactors. Preferably the reaction is carried out at a pressure of about 20 to about 60 lbs./sq. in. The reaction may be carried out in either the liquid state or in the vapor state, however, it is generally advantageous to carry out the process in the liquid state so that the catalyst does not have to be subliminated and so that unduly large reactor equipment is not required. By carrying out the reaction heterogeneously in the liquid state where the reactants are in a liquid state; the catalyst is in the solid state; and the hydrosilane reaction promoter is in the liquid state, the liquid reactants can easily be separated from the solid catalyst so that the solid catalyst can be reused again to react additional quantities of reactants.

The length of time that the residue and the alkyltrihalosilane are in contact with the catalyst and the hydrosilane reaction promoter at an elevated temperature is not critical as long as the redistribution product or products containing halogen-rich disilanes or polysilanes is achieved. Generally, one skilled in the art can determine the optimum reaction time, depending upon the particular reactants, catalysts, reaction promoter, pressure and temperature of the reaction mixture, without undue experimentation. It has been found in most of the preferred embodiments that the residue is contacted with the alkyltrihalosilane in the presence of the catalyst and the reaction promoter for about 0.25 hour to about 7.0 hours to achieve the desired redistribution products. As expressed above, the reaction time will vary as to temperature and pressure. In preferred embodiments, the reaction is carried out at a temperature in the range of about 100° C. to about 175° C. and at a pressure of about 20 to about 60 lbs./sq. in. for a period of about 0.25 hour to about 7 hours and, more preferably, for about 2 hours to about 4 hours. Since the progress of the reaction can be followed by sampling the reaction mixture and making vapor phase chromatography or gas-liquid chromatography measurements thereon to determine the silane, disilane and/or polysilane components therein, it can be easily determined when the desired halogen-rich silanes and/or polysilanes have been produced in the desired or optimum quantity.

The process of the present invention and the redistribution reactions of the present invention may be carried out either in a batch, semi-continuous or continuous manner. Thus, since the hydrosilane reaction promoter is a liquid at the reaction temperatures that are utilized and taught in the present invention for the foregoing redistribution, and since the aluminum trichloride or other catalyst are generally solid at those temperatures, the liquids may simply be passed in the form of gases or liquids into contact with the solid inorganic catalyst for the desired period of time and then taken out in the desired redistributed form. Thus, the introduction of the reactants to be redistributed, that is, the residue, into contact with a hydrosilane reaction promoter also in the vapor or liquid form and the aluminum trichloride as well as the removal of the reaction products may be carried out in a continuous manner by utilizing a column. The utilization of columns in order to carry out similar processes in a continuous manner is well known in the art.

As explained above, the halogen-rich disilanes and/or polysilanes prepared by the process of the present invention can be cleaved into valuable monosilane products. It has been explained above that the chlorine-rich disilanes prepared by redistribution of the alkyl-rich disilanes in residues can be used in a conventional residue cleavage process, for example, by the process disclosed in U.S. Pat. Nos. 2,709,176 and 2,842,580 incorporated herein by reference and discussed in more detail above, or by the hydrogen chloride residue cleavage process well known in the prior art. Thus, the halogen-rich disilanes prepared by the process of the present invention can be separated from the redistribution product and thereafter treated so that the silicon-silicon bond of the disilane is cleaved to form monohalosilanes, or the halogen-rich disilanes prepared by the redistribution process of the present invention can be cleaved in the redistribution product to form halomonosilanes, and the halomonosilanes can be separated from the reaction mixture. The alkyldihalosilane product resulting from the alkyltrihalosilane can also be easily separated from the reaction mixture by any suitable means, for example, by distillation.

In carrying out one mode of the present process, residue from the direct process discussed above, is redistributed with methyltrichlorosilane in the presence of aluminum trichloride catalyst and methyldichlorosilane reaction promoter to form a redistributed product. The redistributed product is distilled to remove the methyldichlorosilane for recycling as well as any other monosilanes found in the redistribution product. The residual chlorine-rich disilanes remaining in the redistributed product after distillation and separation from the solid catalyst are cleaved or fractured by a suitable cleavage process as discussed above. The aluminum trichloride catalyst is recycled for further use as catalyst in redistribution reactions. In another mode, the product from a residue cleavage process is distilled to separate out the methyl-rich disilanes which are then redistributed with methyl-trichlorosilane to obtain chlorine-rich disilanes which can be cleaved or fractured in the residue cleavage process after separation. For example, a residue from a direct process is cleaved using a conventional hydrogen chloride cleavage process to form a cleavage product. The cleavage product is then distilled to separate monosilanes from methyl-rich disilanes. The methyl-rich disilanes are then reacted with methyltrichlorosilane in the presence of dichloromethylsilane reaction promoter and aluminum trichloride catalyst to form a redistribution product. The redistribution product is distilled to remove monosilanes including methyldichlorosilane reaction promoter suitable for recycling from a residue containing chlorine-rich disilanes. The chlorine-rich disilanes are then fractured or cleaved by a conventional residue cleavage process.

In one of the preferred embodiments of the present invention, the process for converting alkyl-rich disilanes in the high boiling residue obtained from the manufacture of methylchlorosilanes to halogen-rich disilanes by a redistribution with methyltrichlorosilane and simultaneously converting the methyltrichlorosilane to dimethyldichlorosilane, comprises, reacting the alkyl-rich disilanes in the residue under substantially anhydrous conditions at a temperature of about 100° C. to about 175° C. in the presence of a catalyst selected from the group consisting of aluminum trichloride, boron trifluoride, zirconium tetrachloride, boric acid, potassium aluminum tetrachloride and cuprous chloride, and a catalytic amount of a hydrosilane reaction promoter selected from the group consisting of methyldichlorosilane, dimethylchlorosilane, phenyldichlorosilane, trichlorosilane, dichlorosilane, monochlorosilane and trimethylsilane.

The process is carried out under anhydrous conditions. Total exclusion of water from the reaction vessel, however, is not required in order to carry out the process of this invention. The residue rapidly reacts with any small amounts of moisture present in the reactor to give a substantially anhydrous reaction environment. Of course, large amounts of moisture can swamp the system producing large amounts of products of hydrolysis which will destroy the catalyst and form undesirable by-products. In any event the exclusion of water and moisture is recommended to the extent that the initial reaction environment contains less than 0.1 percent by weight of water. Thus, although the reaction of the present invention proceeds if atmospheric moisture is present, better yields of desired redistribution products are obtained if moisture is completely excluded from the reaction vessel.

In order that those skilled in the art may better understand how the present invention is practiced, the following examples are presented by way of illustration and not by limitation. Unless it is otherwise shown, all parts are by weight.

EXAMPLE 1

A pressure autoclave was charged with 375 grams of reactants made up of 19% by weight hexamethyldisilane and 81% by weight methyltrichlorosilane along with 58 grams of methyldichlorosilane reaction promoter and 45 grams of aluminum trichloride catalyst. The 1-liter pressure autoclave was sealed, and the contents were heated to 150° C. and held at 150° C. for 1 hour while being agitated. After cooling, the reaction mixture from the autoclave was analyzed by vapor-phase chromatography and found to contain the components set forth in Table I below. In the following tables, Me represents methyl.

TABLE I

Analysis of Reaction Products of Hexamethyldisilane and Methyltrichlorosilane Reacted With Methyldichlorosilane Reaction Promoter and Aluminum Trichloride Catalyst

| Component | Amount (wt. %) |
|---|---|
| (a) Me$_3$SiCl | 4.9 |
| (b) Me$_2$SiCl$_2$ | 49.8 |
| (c) MeSiCl$_3$ | 10.0 |
| (d) Me$_3$SiSiMe$_3$ | None |
| (e) Me$_3$SiSiMe$_2$Cl | None |
| (f) ClMe$_2$SiSiMe$_2$Cl | 3.1 |
| (g) ClMe$_2$SiSiMeCl$_2$ | 17.5 |
| (h) Cl$_2$MeSiSiMeCl$_2$ | 4.3 |

After only 1 hour of reaction time, the data in Table I show that methyl-rich disilanes were converted to chlorine-rich disilanes by redistribution using a chlorine-rich methyldichlorosilane reaction promoter. A substantial amount of valuable product, dimethyldichlorosilane, was found as a component in the reaction mixture after 1 hour, and chlorine-rich disilanes represented by formulas (g) and (h) which are useful in the residue cleavage process to form monosilanes, were formed during the reaction. None of the hexamethyldisilane starting material was found in the reaction product.

EXAMPLE 2

All conditions of Example 1 were repeated except that the reaction components were heated to 100° C. and held at 100° C. in the autoclave. The reaction product was analyzed by vapor phase chromatography and found to contain the components set forth in Table II below.

TABLE II

Analysis of Reaction Products of Hexamethyldisilane and Methyltrichlorosilane Reacted With Methyldichlorosilane Reaction Promoter

| Component | Amount (wt. %) |
|---|---|
| (a) Me$_3$SiCl | 5.4 |
| (b) Me$_2$SiCl$_2$ | 46.6 |
| (c) MeSiCl$_3$ | 11.9 |
| (d) Me$_3$SiSiMe$_3$ | None |
| (e) Me$_3$SiSiMe$_2$Cl | None |
| (f) ClMe$_2$SiSiMe$_2$Cl | 3.8 |
| (g) ClMe$_2$SiSiMeCl$_2$ | 18.2 |
| (h) Cl$_2$MeSiSiMeCl$_2$ | 4.3 |

As in Example 1, the data of Example 2 show that methyl-rich disilanes can be converted to chlorine-rich disilanes by redistribution with a chlorine-rich methylchlorosilane, such as methyltrichlorosilane and at the same time form a useful methylchlorosilane, namely, dimethyldichlorosilane. In both Examples 1 and 2, the hexamethyldisilane was converted to the chlorine-rich disilanes, namely, 1,1,2-trimethyltrichlorodisilane and 1,1,2,2-tetrachlorodimethyldisilane which can be used in conventional residue cleavage processes to form valuable monosilanes. It can also be seen that the product contains 46.6 weight percent dimethyldichlorosilane and only 11.9 weight percent methyltrichlorosilane even though the initial methyltrichlorosilane was 81 weight percent.

EXAMPLE 3

A total of 371 grams of reactants made up of 24% by weight hexamethyldisilane and 76% by weight of methyltrichlorosilane, together with 40 grams of aluminum trichloride, were charged to a 1-liter, sealed, pressure autoclave, and while being agitated, the contents were heated to 150° C. and thereafter held at 150° C. for 3 hours. The pressure in the autoclave was 75 pounds per square inch during the reaction. After 3 hours the contents were cooled, and the reaction mixture was analyzed by vapor phase chromatography and found to contain the components set forth in Table III below:

TABLE III

Analysis of Reaction Products of Hexamethyldisilane and Methyltrichlorosilane Reacted In the Presence of Aluminum Trichloride Catalyst With No Reaction Promoter

| Component | Amount (wt. %) |
|---|---|
| (a) $Me_3SiCl$ | 15.9 |
| (b) $Me_2SiCl_2$ | 8 |
| (c) $MeSiCl_3$ | 59 |
| (d) $Me_3SiSiMe_3$ | None |
| (e) $Me_3SiSiMe_2Cl$ | 7.7 |
| (f) $ClMe_2SiSiMe_2Cl$ | 12.6 |
| (g) $ClMe_2SiSiMeCl_2$ | 0.6 |
| (h) $Cl_2MeSiSiMeCl_2$ | |

The data in Table III illustrate that there is very little chlorine-rich disilane redistribution product designated by components (g) and (h) when no hydrosilane reaction promoter is used in the process. When only aluminum trichloride catalyst is used in the process where hexamethyldisilane and methyltrichlorosilane are used as reactants, only 0.6 weight percent of combined chlorine-rich disilane redistribution products are formed, and a substantial amount of component (c), methyltrichlorosilane, remains in the product mixture. It can be seen that only 17 weight percent of the methyltrichlorosilane was used during the 3 hours of reaction in the autoclave at 150° C. Example 3 illustrates the value of the hydrosilane reaction promoter in the formation of the chlorine-rich disilane redistribution products.

EXAMPLE 4

In this example, a residue taken from the direct process for the manufacture of alkylhalosilanes was used in the autoclave. The residue contained 3.0 weight percent hexamethyldisilane, 4.2 weight percent chloropentamethyldisilane designated herein as methyl-rich disilane as well as 4.3 weight percent 1,2-dichlorotetramethyldisilane. A total of 250 grams of the residue was mixed with 112 grams of methyltrichlorosilane and 40 grams of methyldichlorosilane reaction promoter. This solution together with 94 grams of aluminum chloride was charged to a 1-liter, sealed, pressure-autoclave, and while being agitated, was heated to 150° C. and thereafter held at 150° C. for 3 hours. At the completion of the 3 hour time period, the reaction product was cooled and analyzed by vapor phase chromatography. The analysis showed a complete consumption of the hexamethyldisilane and the chloropentamethyldisilane along with a decrease in the concentration of the 1,2-dichlorotetramethyldisilane from the original amount of 4.3 weight percent to 2.1 weight percent. The concentration of trimethylchlorosilane was 2.1 weight percent, and the concentration of dimethyldichlorosilane was 25 weight percent. Small amounts of the chlorine-rich disilanes, namely, 1,1,2-trichlorotrimethyldisilane and 1,1,2,2-terachloromethyldisilane were also formed. This example illustrates that the methyl-rich disilanes in a residue containing methyl-rich disilanes and obtained from the manufacture of alkylhalosilanes by the direct process can be converted to chlorine-rich disilanes and thereafter can be used in the residue cleavage process. At the same time, valuable and useful methylchlorosilanes, namely, trimethylchlorosilane and dimethyldichlorosilane were formed.

As shown above, the polysilane-containing residue from the direct process for the manufacture of alkylhalosilanes, generally from an alkylhalide and silicon, can be redistributed with methyltrichlorosilane in the presence of an inorganic catalyst and a hydrosilane reaction promoter. In alternative embodiments, the product from a residue cleavage process as described above and in the prior art, can be distilled to separate out the methyl-rich disilanes which are then redistributed with methyltrichlorosilane to obtain chlorine-rich disilanes.

In accordance with the process of the present invention, components of residues which normally would require disposal by incineration or by other means, can be utilized to form useful products. Representative of the compounds which can be converted to desirable products in accordance with the process of the present invention, are the methylrich disilane portions of residues and methyltrichlorosilane.

While the invention has been described with respect to preferred embodiments, it will be apparent that certain modifications and changes can be made without departing from the spirit and scope of the invention, and therefore, it is intended that the foregoing disclosure be limited only by the claims appended hereto.

What is claimed is:

1. A process for treating alkyl-rich disilane-containing residues, comprising contacting the residue with alkyltrihalosilane or silicon tetrahalide in the presence of a catalyst and a catalytic amount of a hydrosilane reaction promoter at an elevated temperature to produce a redistribution product containing halogen-rich disilanes and dialkyldihalosilane.

2. The process of claim 1 further comprising separating the halogen-rich disilanes from the redistribution product.

3. The process of claim 2 further comprising cleaving the silicon-silicon bond of the halogen-rich disilanes to form halosilanes.

4. The process of claim 1 further comprising cleaving the halogen-rich disilanes in the redistribution product to form halosilane and separating halosilane therefrom.

5. The process of claim 1 wherein the temperature is about 100° C. to about 175° C.

6. The process of claims 1 or 5 further comprising subjecting the residue, alkyltrihalosilane and hydrosilane to a pressure greater than atmospheric.

7. The process of claims 1 or 5 further comprising contacting the residue, alkyltrihalosilane and hydrosilane at a pressure of about 1 atmosphere to about 3 atmospheres.

8. The process of claim 1 wherein the alkyltrihalosilane is methyltrichlorosilane.

9. The process of claim 1 wherein the catalyst is a Lewis Acid.

10. The process of claim 9 wherein the catalyst is selected from the group consisting of boric acid, boron trifluoride, zirconium tetrachloride, aluminum trichloride, potassium aluminum tetrachloride and cuprous chloride.

11. The process of claims 1, 9 or 10 wherein the catalyst is used in a concentration of about 1 to about 15% by weight of the reaction mixture.

12. The process of claim 1 wherein the hydrosilane is a monosilicon organic compound containing an Si-H linkage.

13. The process of claims 1 or 5 wherein the residue is contacted with alkyltrihalosilane in the presence of the catalyst and the promoter for about 0.25 hour to about 7.0 hours.

14. The process of claims 1 or 12 wherein the hydrosilane is an alkyldihalohydrosilane.

15. The process of claims 1 or 12 wherein the hydrosilane is methyldichlorosilane.

16. A process for converting an alkyl-rich polysilane in the residue obtained from the manufacture of alkylhalosilane to halogen-rich polysilane with alkyltrihalosilane and simultaneously converting the alkyltrihalosilane to dialkyldihalosilane under substantially anhydrous conditions, comprising reacting the alkyl-rich polysilane in the residue and the alkyltrihalosilane at an elevated temperature in the presence of a suitable catalyst and a catalytic amount of a hydrosilane reaction promoter.

17. The process of claim 16 further comprising separating the halogen-rich polysilane from the residue.

18. The process of claim 16 wherein the temperature is about 100° C. to about 175° C.

19. The process of claims 16 or 18 further comprising carrying out the reaction at a pressure greater than atmospheric pressure.

20. The process of claims 16 or 18 further comprising carrying out the reaction at a pressure of about 1 atmosphere to about 3 atmospheres.

21. The process of claims 16 or 18 comprising carrying out the reaction for about 0.25 hour to about 7.0 hours.

22. The process of claim 16 wherein the catalyst is a Lewis acid.

23. The process of claims 16 or 22 wherein the catalyst is selected from the group consisting of boric acid, boron trifluoride, zirconium tetrachloride, aluminum trichloride, potassium aluminum tetrachloride, and cuprous chloride.

24. The process of claims 16 or 22 wherein the catalyst is used in a concentration of about 1 to about 15% by weight of the reaction mixture.

25. The process of claim 16 wherein the alkyl-rich polysilane is alkyl-rich disilane, the halogen-rich polysilane is a chlorine-rich disilane and the alkyltrihalosilane is methyltrichlorosilane.

26. The process of claims 16 or 25 wherein the alkyltrihalosilane comprises about 0.5 mole to about 4.0 moles per mole of polysilane in the residue.

27. The process of claim 16 wherein the hydrosilane is selected from the group consisting of phenyldichlorosilane, dimethylchlorosilane, methyldichlorosilane, trichlorosilane, dichlorosilane, monochlorosilane and trimethylsilane.

28. The process of claims 16 or 27 wherein the hydrosilane comprises about 0.01 to about 50.0 mole % based upon the amount of moles of the reaction ingredients.

29. The process of claims 16 or 27 wherein the hydrosilane comprises about 1 to about 20 mole % based upon the amount of moles of the reaction ingredients.

30. The process of claim 17 further comprising cleaving the silicon-silicon bonds of the halogen-rich polysilanes to form halosilanes.

31. The process of claim 16 further comprising cleaving the halogen-rich polysilanes obtained by reacting the alkyl-rich polysilane and the alkyl-trihalosilane in the presence of the catalyst and the reaction promoter to form halosilanes and separating halosilanes therefrom.

32. The process of claims 16 or 30 further comprising separating the dialkyldihalosilane from the reaction mixture.

33. A process for converting alkyl-rich disilanes in the high boiling residue obtained from the manufacture of methylchlorosilanes to halogen-rich disilanes by a redistribution with methyltrichlorosilane and simultaneously converting the methyltrichlorosilane to dimethyldichlorosilane, comprising reacting the alkyl-rich disilanes in the residue under substantially anhydrous conditions at a temperature of about 100° C. to about 175° C. in the presence of a catalyst selected from the group consisting of aluminum trichloride, boron trifluoride, zirconium tetrachloride, boric acid, potassium aluminum tetrachloride and cuprous chloride, and a catalytic amount of a hydrosilane reaction promoter selected from the group consisting of methyldichlorosilane, dimethylchlorosilane, phenyldichlorosilane, trichlorosilane, dichlorosilane, monochlorosilane and trimethylsilane.

34. The process of claim 33 comprising carrying out the reaction in an autoclave at a pressure greater than atmospheric pressure.

* * * * *